United States Patent [19]

Tanaka

[11] Patent Number: 4,995,069
[45] Date of Patent: Feb. 19, 1991

[54] X-RAY TUBE APPARATUS WITH PROTECTIVE RESISTORS

[75] Inventor: Shigeru Tanaka, Ootawara, Japan

[73] Assignee: Kabushiki Kaisha Toshiba, Kawasaki, Japan

[21] Appl. No.: 337,821

[22] Filed: Apr. 13, 1989

[30] Foreign Application Priority Data

Apr. 16, 1988 [JP] Japan .................................. 63-94312

[51] Int. Cl.$^5$ ............................................. H01J 35/12
[52] U.S. Cl. ........................................ 378/200; 378/4; 378/101
[58] Field of Search .................... 378/4, 101, 102, 104, 378/141, 121, 127, 150, 151, 200

[56] References Cited

U.S. PATENT DOCUMENTS

| | | | |
|---|---|---|---|
| 2,216,210 | 10/1940 | Mutscheller | 378/104 |
| 3,309,523 | 3/1967 | Dyke et al. | 378/134 |
| 4,117,334 | 9/1978 | Strauts | 378/115 |
| 4,192,997 | 3/1980 | Baumann | 378/101 |
| 4,324,978 | 4/1982 | Kalender et al. | 378/150 |
| 4,651,338 | 3/1987 | Hahn | 378/200 |
| 4,720,844 | 1/1988 | Bougle | 378/104 |
| 4,783,795 | 11/1988 | Yahara | 378/4 |
| 4,856,036 | 8/1989 | Malcolm et al. | 378/116 |

Primary Examiner—Craig E. Church

Attorney, Agent, or Firm—Oblon, Spivak, McClelland, Maier & Neustadt

[57] ABSTRACT

An alternating-current voltage of a commercial power supply is converted to a direct-current voltage by a rectifier and the output direct-current voltage of the rectifier is converted to an alternating-current voltage again by a DC/AC inverter. The alternating-current voltage is boosted by a transformer up to an intermediate voltage (e.g., 1–20 KV). The output voltage of the transformer is supplied through the slip-ring provided between a frame stationary section and a frame rotating section of a voltage multiplier provided within the rotating section to be multiplied to a high voltage (e.g., ±60–±70 KV). Outputs of the voltage multiplier are supplied to the anode and cathode of an X-ray tube. A voltage multiplier for producing an anode supply voltage and a voltage multiplier for producing a cathode supply voltage are constructed in separate units. The two voltage multiplier units and the X-ray tube unit are disposed within a housing of the rotating section shaped like a ring at equal angular intervals of 120°. The X-ray tube unit contains a protective resistor. The protective resistor is connected in at least one of positions between the anode of the X-ray tube and an anode voltage supply terminal, between a center metal of the X-ray tube and a center metal terminal and between the cathode of the X-ray tube and a cathode voltage supply terminal.

26 Claims, 5 Drawing Sheets

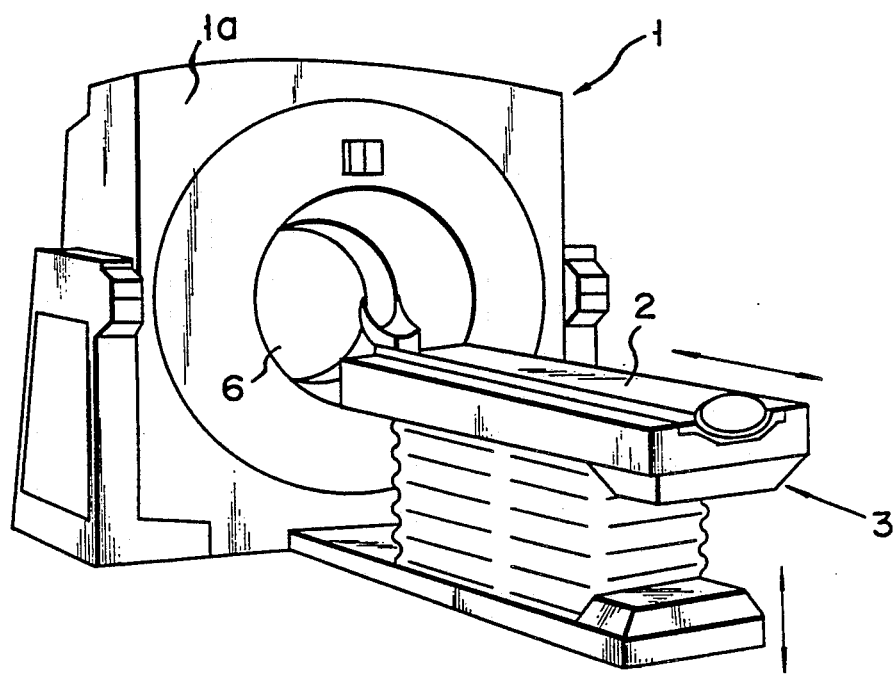
F I G. 2
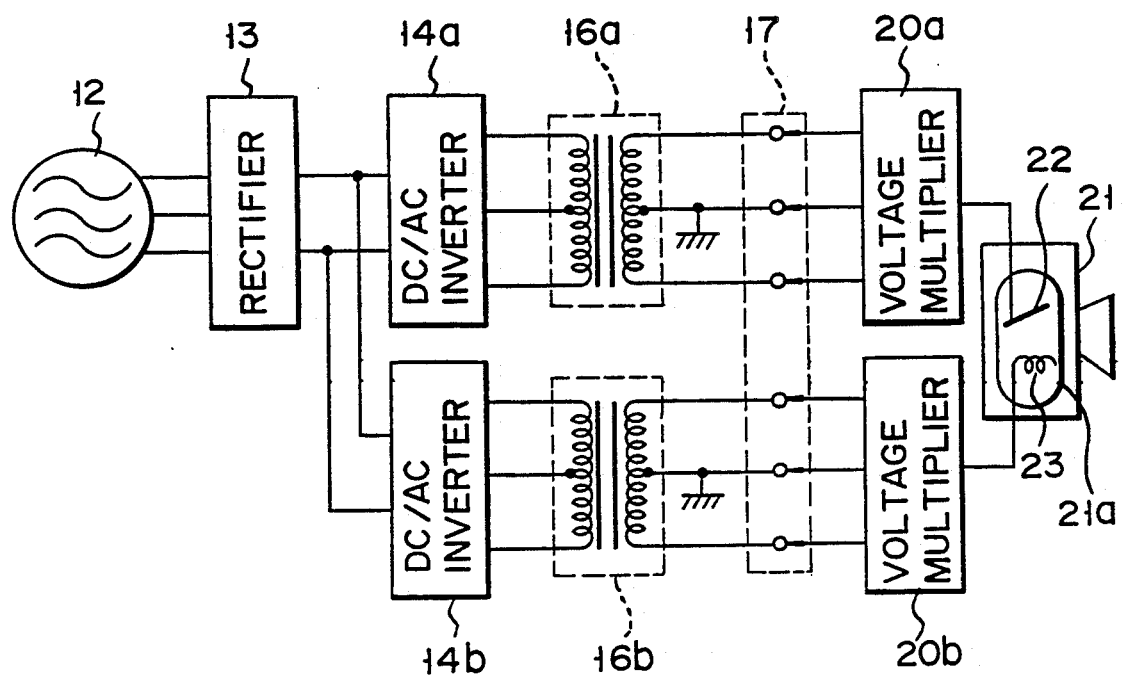
F I G. 3

X-RAY TUBE APPARATUS WITH PROTECTIVE RESISTORS

BACKGROUND OF THE INVENTION

1. Field of the Invention

The present invention relates to an X-ray generating apparatus for use with an X-ray CT scanner.

An example of a conventional X-ray generating apparatus is shown in FIG. 1. An X-ray tube 81 has an anode 82 and a cathode 83. A power-supply device 84 comprises: a high-tension transformer 85 having a primary winding 86 and secondary windings 87 and 88; rectifiers 89 and 91 for rectifying outputs of secondary windings 87 and 88; capacitors 90 and 92 for smoothing outputs of rectifiers 89 and 91; and a filament transformer 93 for supplying power to cathode 83 for heating thereof. Connected between anode 82 and capacitor 90 is a protective resistor (or an impulse resistor) 94 to limit short-circuit current which may flow when abnormal discharge take places in X-ray tube 81. A protective resistor 95 is also connected between cathode 83 and capacitor 92.

With such an arrangement, cathode 83 of X-ray tube 81 is heated by filament transformer 93, and high voltages (e.g., ±75 KV with respect to ground potential) are respectively applied to anode 82 and cathode 83 of X-ray tube 81 via protective resistors 94 and 95 so that thermions emitted by heated cathode 83 impinge upon anode 82 to generate X rays.

Excessive current may flow between the anode and the cathode of X-ray tube 81 because of short-circuiting thereof caused by some abnormality. The current, however, is limited by protective resistors 94 and 95. In other words, the protective resistors are useful for lengthening the life of X-ray tube 81. However, the protective resistors have a high resistance of several kiloohms and is thus large in the amount of heat resulting from current flowing therethrough. For this reason, there is the need for provision of a cooling system using oil or gas, thus disadvantageously making the power-supply device massive. Since there is the need of cooling medium, it is difficult to mold the power supply with resin. In order to reduce a weight and a size of the power-supply device, it is effective to mold the power-supply device using silicon. However, silicon molding results a poor heat-radiation.

The following problems occur when such an X-ray generating apparatus is used with an X-ray CT scanner. In the X-ray CT scanner, generally, an X-ray tube is disposed within a rotating member rotatably supported by a fixed frame, a power-supply device is placed outside the frame, and a high voltage (±75 KV) is supplied from the power-supply device to the rotating member through a high-voltage slip-ring. With such a slip-ring system, there is the need of applying gas insulation or oil insulation to the slip-ring because voltage applied thereto is very high. However, it is very difficult to keep the slip-ring airtight and moreover the slip-ring itself requires a special structure. This will render the slip-ring costly.

Therefore, a low-voltage slip-ring system has been developed in which a high-voltage generator is installed in a rotating member, a low voltage (200–400 V) generated by a commercial power supply is transmitted to the rotating member through a low-voltage slip-ring, and the low voltage s converted to a high voltage (±75 KV) within the rotating member. With such a system, however, since the rotating member must be equipped with the high-voltage generator comprised of a transformer, the frame itself must be made large to stand weight. As described above, the high-voltage generator cannot be made small, light and be molded. It is thus difficult to equip the frame with the high-voltage generator. Moreover, current flow must be the larger because the voltage is low. Since, however, the flow of large current (e.g., 50–200A) through the slip-ring increases the amount of heat generated by the slip-ring, it is necessary to provide a separate heat exchanger so as to prevent heat generation of the ring. In addition, where the rotating member is equipped with the high-voltage generator, the balance of the rotating member will be disturbed because the high-voltage generator is considerably heavy. For this reason, it becomes necessary to add a balance weight to the rotating member so as to keep it in balance. This will make the frame larger and larger.

SUMMARY OF THE INVENTION

It is accordingly an object of the present invention to provide a small and light X-ray generating apparatus which is simple in construction and permits sufficient cooling of protective resistors adapted to limit short-circuit current of an X-ray tube.

It is another object of the present invention to provide a small and inexpensive X-ray CT scanner which eliminates the need for high-voltage withstanding insulation of a slip-ring and moreover permits the reduction of the loadage of a rotating member of a frame.

It is still another object of the present invention to provide an X-ray CT scanner which permits a well-balanced arrangement of components of a power-supply device in a rotating member of a frame without the need for an additional balance weight.

An X-ray generating apparatus according to the present invention comprises an X-ray tube having an anode and a cathode; a protective resistor connected to at least one of the anode and the cathode; and a housing for holding the protective resistor and the X-ray tube together with a cooling medium.

An X-ray CT scanner according to the present invention comprises a housing member for holding an X-ray tube unit having an X-ray tube, a protective resistor for limiting short-circuit current produced at a time of short circuiting of the X-ray tube, and a cooling medium; means for rotatably supporting the housing member around a subject under examination; means for transforming a power supply voltage to a first predetermined voltage; and means for boosting the first voltage to a second voltage that is necessary to drive the X-ray tube. The boosting means is placed within the housing member and the transforming means is placed outside the housing member.

BRIEF DESCRIPTION OF THE DRAWINGS

FIG. 2 is a perspective view of an X-ray CT scanner which is an embodiment of an X-ray tube apparatus according to the present invention;

FIG. 3 is a block diagram of a power-supply device of the X-ray scanner;

DETAILED DESCRIPTION OF THE PREFERRED EMBODIMENTS

Figure 1:
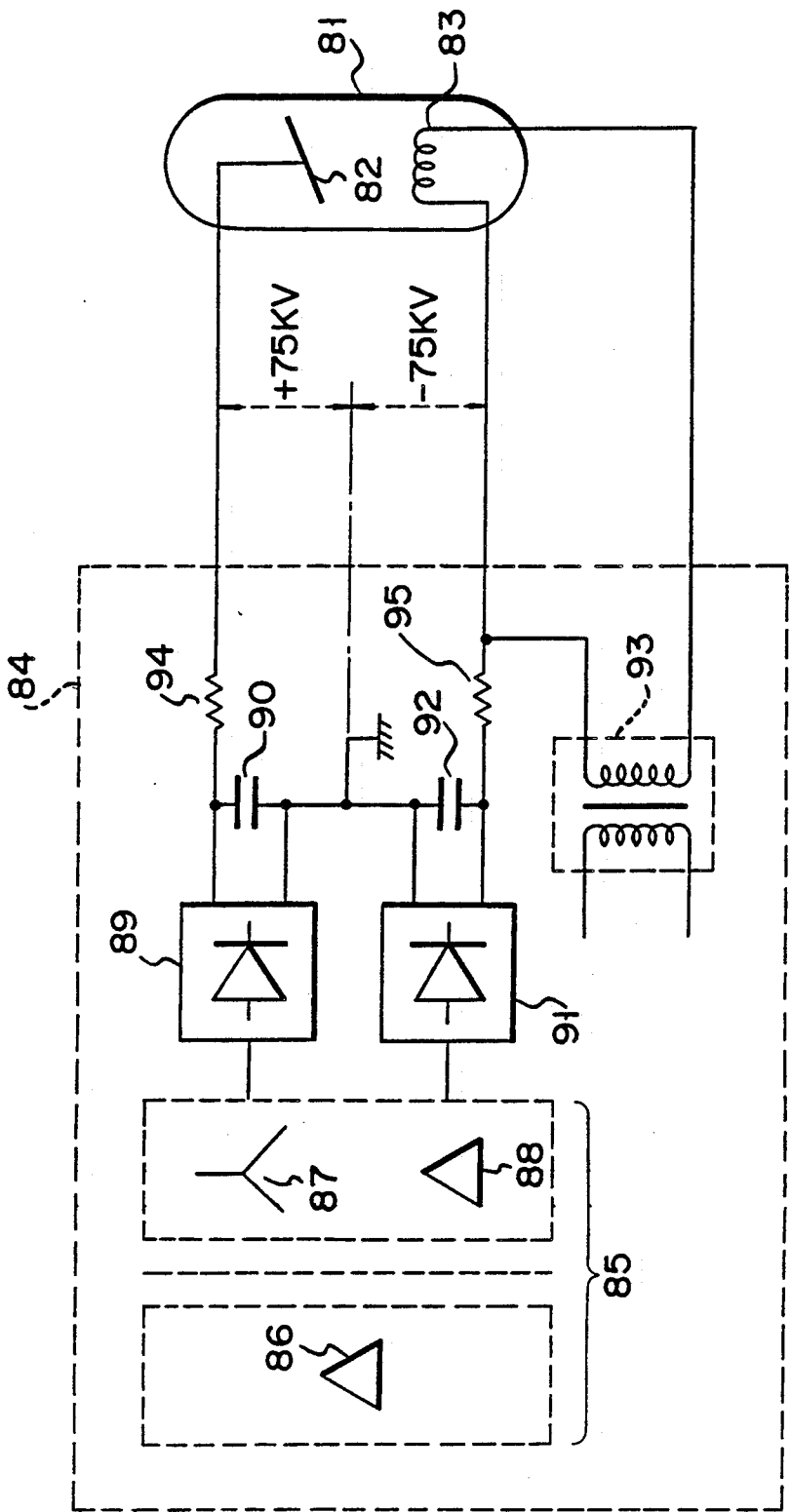
FIG. 1 is a block diagram of a conventional X-ray generating apparatus.

An X-ray CT scanner, which is a first embodiment of the invention, will now described with reference to the drawings attached hereto.

FIG. 2 shows the outer view of the X-ray CT scanner. The X-ray CT scanner has frame 1 and bed 3. Frame 1 has large opening 6. Frame 1 comprises stationary section 1a and a ring-shaped rotating section rotatably supported by the stationary section 1a. Rotating section contains an X-ray tube unit and the like. Rotating section is connected to the stationary section 1a by means of a sliding contact such as a slip-ring, such that a current can be supplied from the stationary section 1a to the rotary section. Bed 2 has a mechanism for moving top plate 2 up and down, and a mechanism for moving top plate 2 in the horizontal direction so that the patient on top plate 2 is moved into and from opening 6 of the frame 1.

FIG. 3 is a block diagram showing a power-supply device which is used in the first embodiment. Commercial power supply 12 supplies a three-phase AC current to rectifier 13. Rectifier 13 changes this AC current into a DC current. The output of rectifier 13 is connected to two power-supply systems. The first system is designed to apply a positive high-voltage to anode 22 of X-ray tube 21a, and the second system is designed to apply a negative high-voltage to cathode 23 of X-ray tube 21a. The current supplied from power supply 12 is not limited to a three-phase AC current. It can either be a single-phase AC current or a DC current. When a DC current source is used, the device does not require rectifier 13.

The DC output of rectifier 13 is supplied to DC/AC inverters 14a and 14b incorporated in the first and second power-supply systems, respectively. Either DC/AC inverter changes the DC voltage to an AC voltage e.g. 200 V) having a predetermined frequency. The AC voltage output by DC/AC inverter 14a is applied to transformer 16a, and the voltage output by DC/AC inverter 14b is applied to transformer 16b. Either transformer boosts the input voltage to an intermediate voltage (e.g. 1 to 20 KV).

AC power supply 12, rectifier 13, inverters 14a and 14b, and transformers 16a and 16b are arranged outside frame 1 or within the stationary section 1a of frame 1, whereas X-ray tube unit 21 and voltage multipliers 20a and 20b are arranged within the rotating section of frame 1. Therefore, the intermediate voltages output from the secondary windings of transformers 16a and 16b are applied to voltage multipliers 20a and 20b, respectively, through a sliding contact, such as a slip-ring 17 interposed between the stationary section 1a and the rotating section. Voltage multipliers 20a and 20b respectively generate a high voltage of, for example, +60 to +70 KV and a high voltage of, for example, −60 to −70 KV. During the warming-up, ±40 to ±75 KV is generated. The positive voltage from multiplier 20a is applied to anode 22 of X-ray tube 21a, and the negative voltage from multiplier 20b is applied to cathode 23 of X-ray tube 21a. X-ray tube unit 21 emits a fan-shaped X-ray beam to the patient. Slip-ring 17 comprises two concentric rings respectively connected to stationary section 1a and rotating section, and a brush mounted on one of these rings and electrically connecting the two rings.

Figure 4:
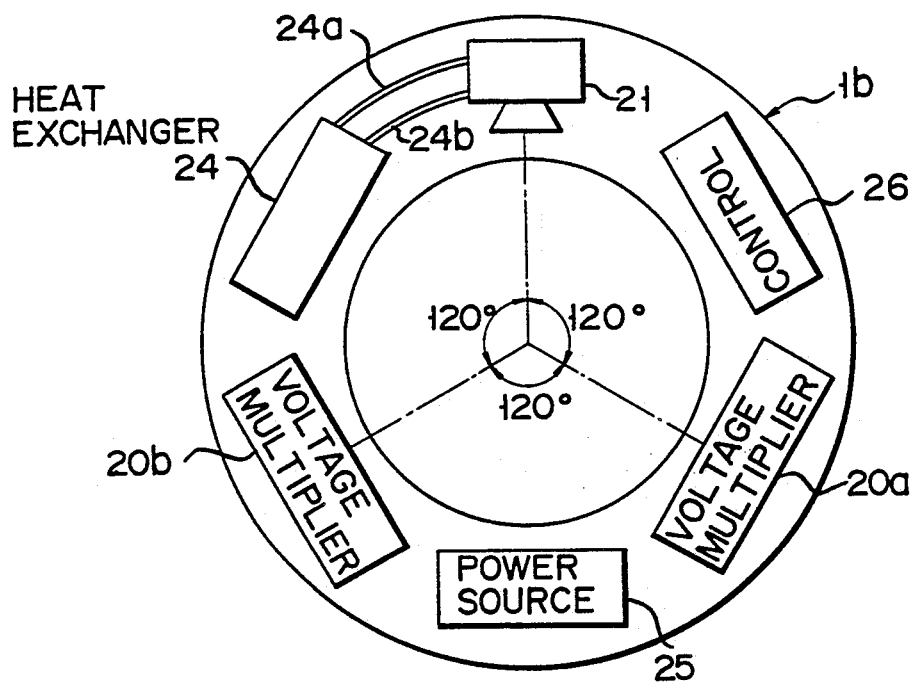
FIG. 4 illustrates an arrangement of component units in a rotating member of the X-ray scanner.

Voltage multiplier 20a for generating the anode voltage of X-ray tube 21a, and voltage multiplier 20b for generating the cathode voltage of X-ray tube 21a are separate components which operate independently of each other. The component including multiplier 20b also has a heater circuit (not shown) for heating cathode 23 of X-ray tube 21. As is shown in FIG. 4, they are located within the ring-shaped housing of rotating section 1b, at equal distance from each other. The X-ray CT scanner illustrated in FIG. 4 is of the so-called fourth generation. Voltage multiplier 20a and 20b, and X-ray tube unit 21, all incorporated within the ring-shaped housing, are positioned at angle intervals of 120°. Further, heat exchanger 24 for X-ray tube unit 21, power source 25, and control section 26 driven by the power supplied from source 25 are arranged also in the housing, among voltage multiplier 20a and 20b and X-ray tube unit 21. More specifically, X-ray tube unit 21, control section 26, voltage multiplier 20a, power source 25, voltage multiplier 20b, and heat exchanger 24 are arranged in a circle in this order, spaced apart from one another at angle intervals of 60°.

Figure 5:
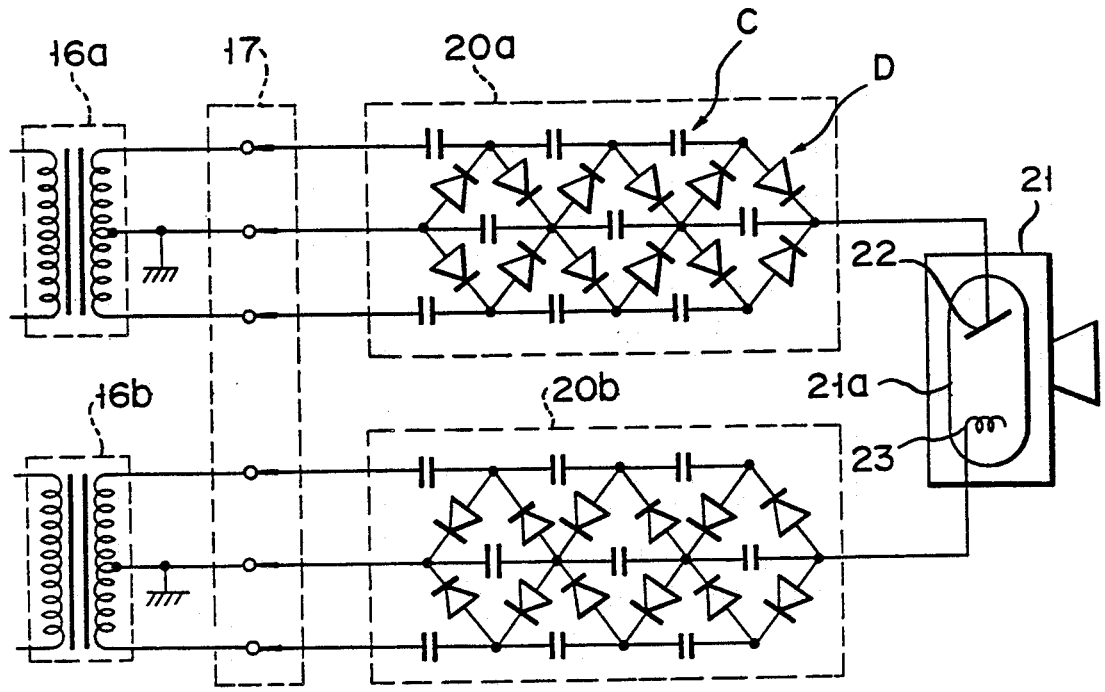
FIG. 5 is a schematic diagram of a voltage multiplier of the X-ray scanner.

Either voltage multipliers (20a, 20b) is the Cockcroft-Walton circuit shown in FIG. 5. The Cockcroft-Walton circuit comprises bridge circuits each consisting of diodes D and capacitors C which are connected as is illustrated in FIG. 5. Voltage multipliers 20a and 20b generate a high-voltage required for X-ray exposure, when the voltage output from the secondary winding of the transformer (16a, 16b) is applied to their input terminals through slip-ring 17. This high-voltage is applied between anode 22 cathode 23 of X-ray tube 21a. More specifically, a voltage of +60 to +70 KV is applied to anode 22 and a voltage −60 to −70 KV is applied to cathode 23 of X-ray tube 21a. Heat exchanger 24 is connected to X-ray tube unit 21 by means of oil hoses 24a and 24b to radiate heat from the insulation oil which is used as cooling medium for the X-ray tube. Control section 26 controls an X-ray optical system (not shown) to adjust the diameter of the X-ray beam which X-ray tube unit 21 emits to the subject.

Voltage multipliers 20a and 20b weight about 30 Kg each. X-ray tube unit 21 also weights about 30 Kg. Heat exchanger 24, power source 25, and control section 26 weights equally, about 15 Kg. Further, as has been described, these components 21, 26, 20a, 25, 20b, and 24 are arranged in a circle, spaced apart from one another at angle intervals of 60°. Hence, rotating section 1b is balanced well. The X-ray CT scanner shown in FIG. 2, which is of the fourth generation, has an X-ray detector (not shown) which is shaped like a ring and incorporated in the stationary section 1a.

Figure 6:
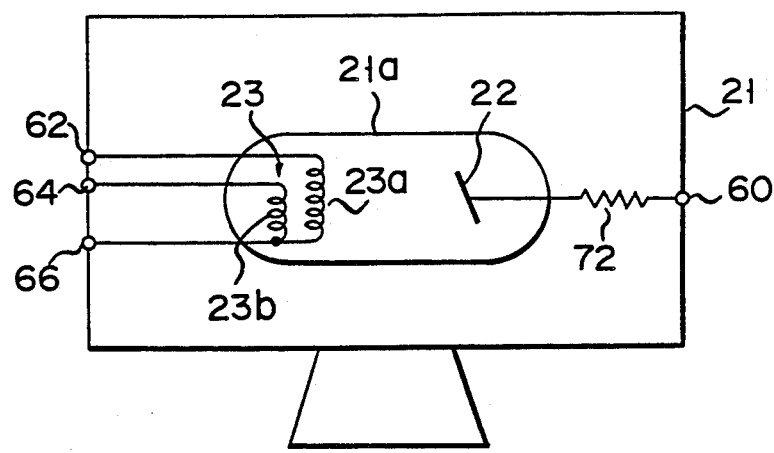
FIGS. 6 through 8 show examples of an X-ray tube unit of the X-ray scanner.

Next, the arrangement of X-ray tube unit 21 will be described. As shown in FIG. 6, the housing of X-ray tube unit 21 is provided with an anode high-voltage supply terminal (referred to as an anode terminal hereinafter) 60 which is connected to voltage multiplier 20a. Connected between anode 22 and anode terminal 60 is a protective resistor 72 of several kiloohms, which limits short-circuit current produced when the X-ray tube abnormally discharges. Being provided in the tube current path, protective resistor 72 can limit the short-circuit Current of the X-ray tube. Cathode 23 comprises first and second filaments 23a and 23b having their ends connected together and the other ends connected to cathode-heating power supply terminals (referred to as cathode heating terminals hereinafter) 62 and 64 which are connected to the heater circuit. This X-ray tube 21a is called the two-focal-point type in which the focal point can be switched between a large focal point and a small focal point by switching current supply from one of filaments 23a and 23b to the other. The ends of filaments 23a and 23b which are connected together are connected to a terminal 66 which is connected to the heater circuit and voltage multiplier 20b. Terminal 66 is used as a cathode heating terminal and moreover as a cathode high-voltage supply terminal (referred to as the cathode terminal hereinafter) for supplying a high voltage to the cathode. Note that, though not shown, the housing for X-ray tube unit 21 is filled with a cooling medium, such as an insulation oil.

As described above, since X-ray tube unit 21 has protective resistor 72 within, there is no need for provision of the protective resistor in the power-supply device. For this reason, the power-supply device is free from a problem of heat generation and hence can be molded and made small and light. The power-supply device may be installed in any position, even in a rotating member. Moreover, since X-ray tube unit 21 is filled with a cooling medium for X-ray tube 21a, e.g., insulation oil, protective resistor 72 within X-ray tube unit 21 can readily be cooled by the insulation oil. This eliminates the special need for a cooling system for the protective resistor.

Figure 7:
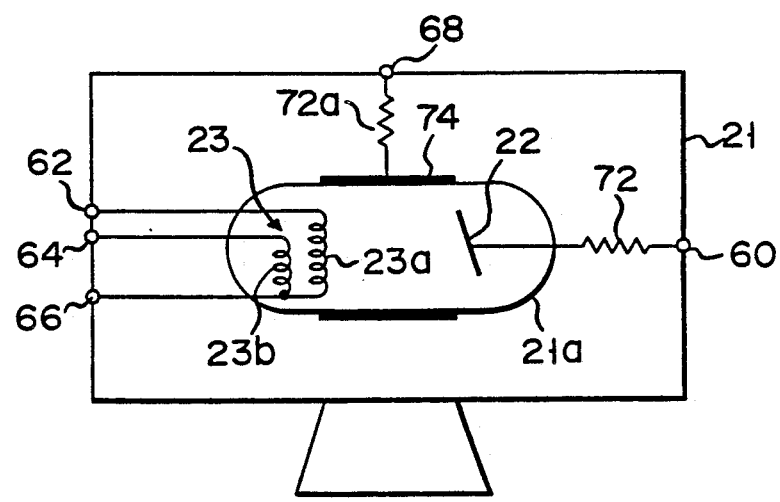

The place of connection of the protective resistor is not limited to the above place. In general, large capacity X-ray tube 21a has a center metal 74 as shown in FIG. 7. Center metal 74 is usually grounded directly via a center metal terminal 68 on the housing of X-ray tube unit 21. Protective resistor 72a may be connected between center metal 74 and center metal terminal 68. Then, even though protective resistor 72 connected to anode 22 is excluded, short-circuit currents resulting from discharges between anode 22 and center metal 74 and between cathode 23 and center metal 74 will be limited by protective resistor 72a. Of course, the provision of protective resistor 72 in addition to protective resistor 72a is more effective because the short-circuit current flowing between anode 22 and cathode 23 can be limited by protective resistor 72.

Figure 8:
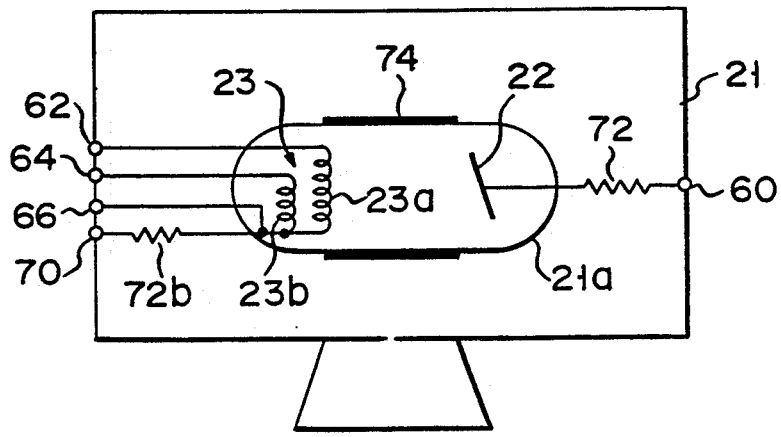

Furthermore, as shown in FIG. 8, a protective resistor 72b may be provided on the side of cathode 72b. In this case, however, if the protective resistor were connected between one end of cathode 23 (filament 23a or 23b) and the cathode heating terminal, the cathode heating current (filament current) would be limited. To avoid this, a cathode terminal 70 is provided in addition to cathode heating terminals 62, 64 and 66 and is connected to the voltage multiplier 20b, and protective 70 and cathode 23. Then, the short-circuit current can be limited without limiting the cathode heating current. Even though protective resistor 72 is excluded, the short-circuit currents resulting from discharges between anode 22 and cathode 23 and between center metal 74 and cathode 23 can be limited by protective resistor 72b. The provision of protective resistors 72 is more effective because the short-circuit current resulting from the discharge between anode 22 and center metal 74 can be limited.

As described above, the protective resistor or resistors may be provided in any of the above positions.

The operation of the embodiment described above will now be explained. First, the top plate 2 of bed 3 is moved up or down until the subject on top plate 2 is positioned at the center of the rotating section. Then, top plate 2 is inserted into the opening 6 of frame 1. The rotating section is rotated such that X-ray tube 21 rotates around the subject.

Meanwhile, rectifier 13 rectifies the AC output supplied from commercial power supply 12, thereby supplying a DC output to DC/AC inverters 14a and 14b. Either DC/AC inverter produces a switching output. Transformers 16a and 16b change the switching outputs of inverters 14a and 14b to intermediate voltages. These voltages are applied via slip-ring 17 to voltage multipliers 20a and 20b. Voltage multipliers 20a and 20b generate a high voltage. The high voltage is applied between the anode 22 and cathode 23 of X-ray tube 21. Thus, X-ray tube 21 is driven by the high voltage and emits an X-ray beam onto the subject, thereby to obtain projection data from the X-rays passing through the subject.

As has been pointed out, the voltage applied from commercial power supply 12 is applied in the form of an intermediate voltage to the rotation section through slip-ring 17, and is converted into a high voltage by means of voltage multipliers 20a and 20b within the rotation section. Therefore, no measures need to be taken to insulate slip-ring 17 as is required in the conventional power-supply device of the high-voltage slip-ring type, nor must any measures be taken to seal insulation medium. For the same reason, no current as great as 50 to 200 A flows through slip-ring 17 as in the conventional power-supply device of the low-voltage slip-ring type. In effect, a small current of about 5 to 20 A flows via slip-ring 17. The heat which slip-ring 17 generates is so small that a heat exchanger need not be provided for radiating this heat thereby to cool slip-ring 17. As a result, slip-ring 17 can be easily manufacture at low cost.

Moreover, since voltage multipliers 20a and 20b are located in the rotating section and comprised of Cockcroft-Walton circuits each made of a few diodes and a few capacitors, they are not only small but light. It is thus unnecessary to make the stationary section large, which supports the rotating section. Therefore, the size of frame 1 can be reduced, helping to decrease the manufacturing cost of the X-ray CT scanner.

As has been described, voltage multipliers 20a and 20b are independent units, and they and X-ray tube unit 21 are arranged in a circle within the rotating section, spaced apart at angle intervals of 120°. Thus, the rotating section is balanced well even if voltage multipliers 20a and 20b and X-ray tube unit 21 are considerably heavy. No balancing weights are required to balance the rotating section. This helps much to reduce the weight of frame 1 as a whole.

Figure 9:
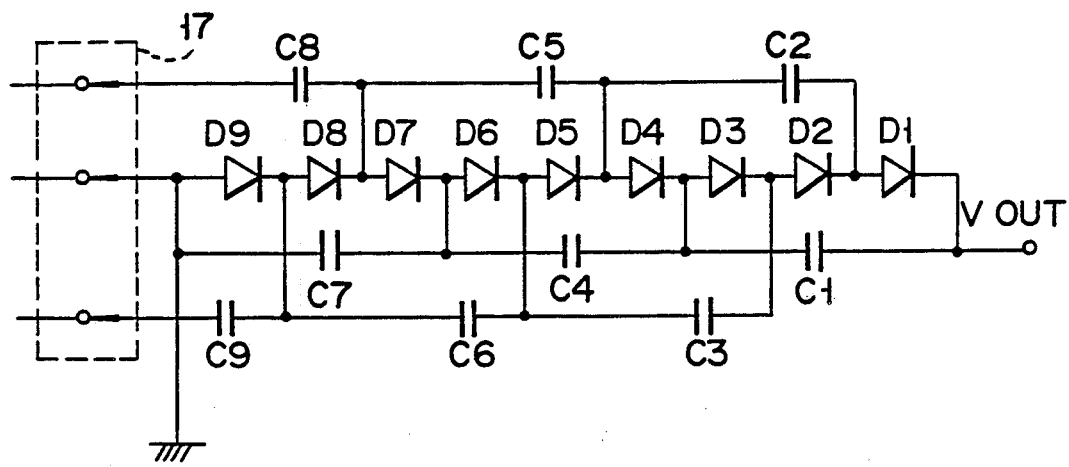
FIG. 9 shows a modification of the voltage multiplier.

A modifications of the present invention will now be described. FIG. 9 shows a modification of the voltage multiplier. The circuit of FIG. 9 comprises diodes D1 to D9 and capacitors C1 to C9.

Figure 10:
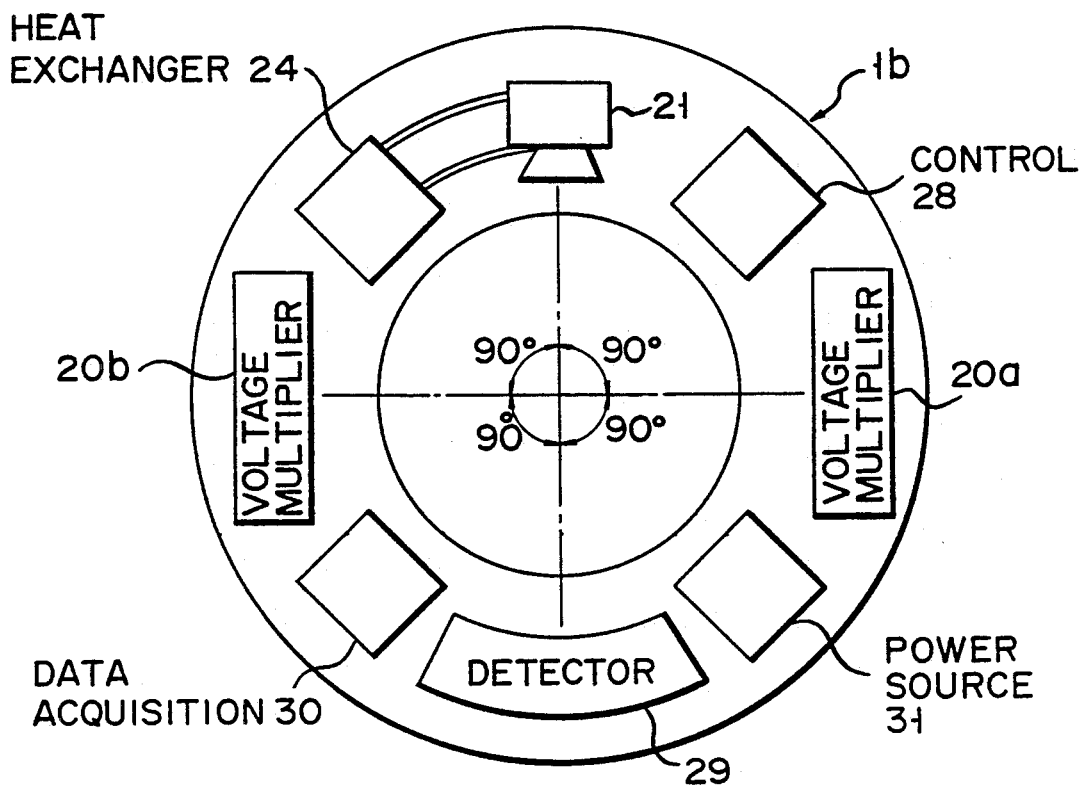
FIG. 10 illustrates an arrangement of component units of a rotating member modified to suit a CT scanner of the third generation.

The present invention can apply to a third-generation X-ray CT scanner. FIG. 10 illustrates how the components of a third-generation X-ray CT scanner are arranged within rotating section 1b. As is shown in this figure, voltage multipliers 20a and 20b, X-ray tube unit 21, heat exchanger 24, control section 28, X-ray detector 29, data acquisition unit 30, and power source 31 are provided within rotating section 1b. Control section 28 is identical to control section 26 used in the first embodiment (FIG. 4). Power source 31 supplies power to unit 30 and section 26. Voltage multipliers 20a and 20b, X-ray tube unit 21, and X-ray detector 29, each weighing about 30 Kg, are arranged in a circle, spaced apart from one another at angle intervals of 90°. Heat exchanger 24, control section 28, data acquisition unit 30 and, power source 31, each of which weights 15 Kg, are located among components 20a, 20b, 21, and 29 and spaced apart from one another at angle intervals of 90°. Thus, rotating section 1b is balanced well as in the first embodiment.

As has been explained, according to the present invention, the transformer converts the voltage applied from a commercial power supply, into an intermediate voltage, and this intermediate voltage is applied from a stationary section to a rotating section of the frame through a slip-ring. Therefore, the slip-ring need not be insulated so as to have a high withstand voltage. Nor must the slip-ring have such a structure as to be easily cooled. Hence, the slip-ring can be produced at low cost. Further, since the high-voltage generator incorporated in the rotating section is a voltage multiplier comprised of only diodes and capacitors, it is simple and light. The load on the rotating section is small, and this section can thus be made small. Therefore, the power-supply device of the invention can be manufactured at low cost. Furthermore, the components of the device can be arranged in the rotating section such that the rotating section is balanced well, and no balancing weights are required to balance this section.

What is claimed is:

1. An X-ray tube apparatus comprising:
   an X-ray tube having an anode and a cathode;
   a protective resistor connected to at least one of said anode and said cathode;
   a power supply coupled to said X-ray tube and said resistor; and housing means for housing said X-ray tube and said protective resistor immersed in an insulating oil, said power supply being outside said housing means.

2. An apparatus according to claim 1, in which said X-ray tube further has a center metal positioned between the anode and the cathode at a peripheral wall of the X-ray tube and said protective resistor is connected to at least one of said anode, said cathode, and said center metal.

3. An apparatus according to claim 1, in which said housing means has an anode terminal for applying a high-voltage to said anode and said protective resistor is connected between said anode and said anode terminal.

4. An apparatus according to claim 1, in which said housing means has a cathode terminal for applying a high-voltage to said cathode and said protective resistor is connected between said cathode and said cathode terminal.

5. An apparatus according to claim 2, in which said housing means has a center metal terminal for connecting said center metal to a ground potential and said protective resistor is connected between said center metal and said center metal terminal.

6. A power-supply apparatus for use in an X-ray CT scanner, said apparatus comprising:
   an X-ray tube unit having an X-ray tube, a protective resistor for limiting a short-circuit current of said X-ray tube, and a housing member in which said X-ray tube and said resistor are housed immersed in an insulating oil;
   support means supporting said housing member such that said housing member moves around a subject;
   power supply means located outside said housing member, for transforming a power-supply voltage into a first voltage; and
   voltage-multiplying means provided at said housing member, for multiplying the first voltage to a second voltage high enough to drive the X-ray tube.

7. An apparatus according to claim 6, in which said X-ray tube further has a center metal positioned between the anode and the cathode at a peripheral wall of the X-ray tube and said protective resistor is connected to at least one of said anode, said cathode, and said center metal.

8. An apparatus according to claim 7, in which said housing member has a center metal terminal for connecting said center metal to a ground potential and said protective resistor is connected between said center metal and said center metal terminal.

9. An apparatus according to claim 8, in which said power supply means is located outside not only said housing member but also said support means, and said power supply means comprises:
   rectifier means for changing an AC output supplied by a commercial power-supply, into a DC output;
   inverter means for converting the DC output supplied by said rectifier means, into an AC output having a desired frequency; and
   transformer means for increasing the AC output voltage supplied by said inverter means to said first voltage which ranges from 1 to 20 KV.

10. An apparatus according to claim 8, in which said voltage-multiplying means is located within said housing member and comprises Cockcroft-Walton circuits, and said second voltage ranges from ±60 to ±70 KV.

11. An apparatus according to claim 8, in which said X-ray tube has an anode and a cathode and said protective resistor is connected to at least one of said anode and said cathode.

12. An apparatus according to claim 11, in which said housing member has a cathode terminal for applying a high-voltage to said cathode and said protective resistor is connected between said cathode and said cathode terminal.

13. An apparatus according to claim 11, in which said housing member has an anode terminal for applying a high-voltage to said anode and said protective resistor is connected between said anode and said anode terminal.

14. An X-ray CT apparatus comprising:
   a ring member including an X-ray tube unit having an X-ray tube and a protective resistor for limiting a short-circuit current of said X-ray tube, and a housing member in which said X-ray tube and said resistor are housed immersed in an insulation oil, the ring member having an opening into which a subject is guided;
   support means supporting said ring member such that said ring member rotates around a subject;
   power supply means located outside said ring member, for transmitting a power-supply voltage into a first voltage; and
   voltage-multiplying means provided at said ring member, for multiplying the first voltage to a second voltage high enough to drive the X-ray tube.

15. An apparatus according to claim 14, in which said power supply means is located outside not only said ring member but also said support means, and comprises:
- rectifier means for changing an AC output supplied by a commercial power-supply, into a DC output;
- inverter means for converting the DC output supplied by said rectifier means, into an AC output having a desired frequency; and
- transformer means for increasing the AC output voltage supplied by said inverter means to said first voltage which ranges from 1 to 20 KV.

16. An apparatus according to claim 14, in which said voltage-multiplying means is located within said ring member and comprises Cockcroft-Walton circuits, and said second voltage ranges from ±60 to ±70 KV.

17. An apparatus according to claim 14, in which said support means supports said ring member by using a slip-ring.

18. An apparatus according to claim 14, in which said voltage-multiplying means comprises a first voltage-multiplying unit for applying a voltage to the anode of said X-ray tube, and a second voltage-multiplying unit for applying a voltage to the cathode of said X-ray tube; and said X-ray tube, said first voltage-multiplying unit, and said second voltage-multiplying unit are arranged within said ring member at regular intervals.

19. An apparatus according to claim 18, which further comprises a heat exchanger for radiating heat from said X-ray tube unit, an X-ray system control section, and a power source for the control section, and in which said X-ray tube unit, said first voltage-multiplying unit, said second voltage-multiplying unit, said heat exchanger, said system control section, and said power source are arranged at regular intervals.

20. An apparatus according to claim 18, which further comprises an X-ray detector, and in which said voltage-multiplying means comprises a first voltage-multiplying unit for applying a voltage to the anode of said X-ray tube, and a second voltage-multiplying unit for applying a voltage to the cathode of said X-ray tube; and said X-ray tube, said first voltage-multiplying unit, second voltage-multiplying unit, and said X-ray detector are arranged within said ring member at regular intervals.

21. An apparatus according to claim 20, which further comprises a heat exchanger for radiating heat from said X-ray tube, an X-ray system control section, a data acquisition unit, and a power source for the control section, and in which said X-ray tube, said first voltage-multiplying unit, said second voltage-multiplying unit, said X-ray detector, said heat exchanger, said system control section, said data acquisition unit, and said power source are arranged at regular intervals.

22. An apparatus according to claim 14, in which said X-ray tube has an anode and a cathode and said a protective resistor is connected to at least one of said anode and said cathode.

23. An apparatus according to claim 22, in which said housing member has an anode terminal for applying a high-voltage to said anode and said protective resistor is connected between said anode and said anode terminal.

24. An apparatus according to claim 22, in which said housing member has a cathode terminal for applying a high-voltage to said cathode and said protective resistor is connected between said cathode and said cathode terminal.

25. An apparatus according to claim 22, in which said X-ray tube further has a center metal positioned between the anode and the cathode at a peripheral wall of the X-ray tube and said protective resistor is connected to at least one of said anode, said cathode, and said center metal.

26. An apparatus according to claim 25, in which said housing member has a center metal terminal for connecting said center metal to a ground potential and said protective resistor is connected between said center metal and said center metal terminal.

* * * * *